US007273932B1

(12) United States Patent
LaBarbera et al.

(10) Patent No.: US 7,273,932 B1
(45) Date of Patent: Sep. 25, 2007

(54) ANTISENSE OLIGONUCLEOTIDES FOR FERTILITY AND MENSTRUAL CYCLE REGULATION AND FOR CHEMOPREVENTIVE AND CHEMOTHERAPEUTIC USE

(75) Inventors: Andrew R. LaBarbera, Cincinnati, OH (US); YiFang Wang, Ottawa (CA); ChangHong Zhu, Hubei (CN)

(73) Assignee: The University of Cincinnati, Cincinnati, OH (US)

( * ) Notice: Subject to any disclaimer, the term of this patent is extended or adjusted under 35 U.S.C. 154(b) by 0 days.

(21) Appl. No.: 10/018,716

(22) PCT Filed: May 16, 2000

(86) PCT No.: PCT/US00/13488

§ 371 (c)(1),
(2), (4) Date: Mar. 28, 2002

(87) PCT Pub. No.: WO00/73416

PCT Pub. Date: Dec. 7, 2000

Related U.S. Application Data

(60) Provisional application No. 60/158,612, filed on Oct. 8, 1999, provisional application No. 60/136,489, filed on May 28, 1999.

(51) Int. Cl.
| | |
|---|---|
| A61K 48/00 | (2006.01) |
| A61K 31/66 | (2006.01) |
| A61K 9/127 | (2006.01) |
| A61K 39/395 | (2006.01) |
| C07H 21/02 | (2006.01) |
| C07H 21/04 | (2006.01) |

(52) U.S. Cl. .................... 536/24.5; 514/44; 424/178.1; 424/450
(58) Field of Classification Search .................... None
See application file for complete search history.

(56) References Cited

U.S. PATENT DOCUMENTS 5,744,448 A    4/1998 Kelton et al.
5,801,154 A *  9/1998 Baracchini et al. ........... 514/44
5,872,206 A *  2/1999 Liang et al. ................ 530/300
6,080,727 A *  6/2000 Zupi ........................... 514/44

FOREIGN PATENT DOCUMENTS

| WO | WO 199104753 | * 3/1991 |
| WO | WO93/20199 | 10/1993 |
| WO | WO97/11194 | 3/1997 |

OTHER PUBLICATIONS

Changhong et al, Antisense Oligonucleotide Inhibits Expression of Recombinant Porcine Follicle-Stimulation Hormone Recepotr, J Tongi Medical University, 1999, vol. 19(3) pp. 175-180.*
Kleisch et al , FSH receptor mRNA is expressed stage-dependetly during rat spermatigoenesis, Molecular and Cellular Endocrinology, 1992, vol. 84, pp. R45-R49.*
Bennett and Cowsert; Antisense oligonucleotides as a tool for gene functionalization and target validation, Biochimica et Biophysica Acta, 1999, pp. 19-30.*
Slootstra and Roubos, Two-receptor binding regions of human FSH show sense-antisense similarity to the human FSH receptor, Biochemical and Biophysical Research Communications, 1991, vol. 179, No. 1, pp. 266-271.*
Gromoll et al, Structure and Organization of the Human Follicle-Stimulating Hormone Receptor (FSHR) Gene, Genomics, 1996, vol. 35, pp. 308-311.*

\* cited by examiner

*Primary Examiner*—Scott D. Priebe
*Assistant Examiner*—Maria B Marvich
(74) *Attorney, Agent, or Firm*—Frost Brown Todd LLC

(57) ABSTRACT

The invention relates to antisense oligonucleotides, in particular to antisense oligonucleotides to receptor genes, and the use of such oligonucleotides to regulate reproductive function and as chemopreventive or as a chemotherapeutic for various cancers, especially ovarian cancers. The invention also provides a method for preventing estrogen synthesis, a function of developing ovarian follicles, a therapeutic consideration for the prevention and treatment of some cancers of the breast, endometrium, ovary and cervix and of some endometriosis. The invention also relates to pharmaceutical compositions containing antisense oligonucleotides (ODNs, having 8 to 60 nucleotides) that act by binding to intracellular molecular targets. Optionally, for efficient delivery to a target DNA, RNA or protein, the ODNs may be covalently linked to a carrier moiety, which facilitates delivery of the ODN to the cytosol.

25 Claims, 2 Drawing Sheets

ANTISENSE OLIGONUCLEOTIDES FOR FERTILITY AND MENSTRUAL CYCLE REGULATION AND FOR CHEMOPREVENTIVE AND CHEMOTHERAPEUTIC USE

This application claims benefit to provisional applications 60/136,489 filed May 28, 1999 and 60/158,612 filed Oct. 8, 1999.

The invention described herein was supported in part by National Institutes of Health grant 1R01HD30370. The United States Government has certain rights in the invention.

FIELD OF THE INVENTION

The invention relates to antisense oligonucleotides, in particular to antisense oligonucleotides to receptor genes, and the use of such oligonucleotides for regulating reproductive function, for regulate estrogen synthesis, for use as a therapeutic, e.g., as chemopreventive or as a chemotherapeutic for various cancers, especially ovarian cancers, for menstrual cycle regulation, and for the management of clinical states of menstrual irregularity, menstrual dysfunction, and menopausal dysfunction. The invention also relates to pharmaceutical compositions containing antisense oligonucleotides (ODNs, having 8 to 60 nucleotides) that act by binding to intracellular molecular targets. Optionally, for efficient delivery to a target DNA, RNA or protein, the ODNs may be covalently linked to a carrier moiety, which facilitates delivery of the ODN to the cytosol.

BACKGROUND OF THE INVENTION

Antisense Oligodeoxynucleotides

The specific hybridization of an oligomeric compound with its target nucleic acid interferes with the normal function of the nucleic acid. This modulation of function of a target nucleic acid by compounds that specifically hybridize to it is generally referred to as "antisense". The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of the target gene. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

Once one or more target sites have been identified, oligonucleotides are chosen which are sufficiently complementary to the target, i.e., hybridize sufficiently well and with sufficient specificity, to give the desired effect.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

Antisense oligodeoxynucleotides (ODNs) provide a means to specifically inhibit synthesis of distinct proteins within a cell. For a review, reference is made to Uhlmann, E. and Peyman, A., (1990) Antisense oligonucleotides: a new therapeutic principle, Chem. Rev., 90, 543, incorporated herein in its entirety. Synthetic antisense oligodeoxynucleotides (ODNs) represent a new tool for the discovery of physiological mechanisms in cell cultures, in tissues and in vivo. Ideally, an antisense ODN is targeted in a sequence-specific manner to nucleic acids to offer the exciting possibility of selectively blocking the expression of a particular gene, and then preventing the translation of messenger RNA (mRNA) into protein without changing the expression of other genes (Askari F K, McDonnell W M 1996 Antisense-oligonucleotide therapy. N Engl J Med 334:316-318.). Although the spectrum of actions of antisense ODNs is probably not totally established, hybridization arrest of translation is the most obvious (Helene C, Toulme J J, 1990 Specific regulation of gene expression by antisense, sense and antigene nucleic acids. Biochim Biophys Acta 1049:99-125.). Translational arrest, the antisense ODN interference in protein synthesis, is possible via different pathways that are determined by the target mRNA sequence. One often chosen target is the region upstream and downstream from the initiation codon AUG coding for methionine (Marcus-Sekura C J, 1988, Techniques for using antisense oligodeoxyribonucleotides to study gene expression. Anal Biochem 172:289-295.), but the CAP site and coding region have also been chosen for successful repression of translation. It is assumed that antisense ODNs binding will interfere with the formation of a translation initiation complex and thus block protein synthesis. Another possibility of obstructing gene expression could be by targeting splice junctions and so interfere in RNA maturation from heterogeneous nuclear RNA (hnRNA) to mRNA in the cell nucleus.

RNase H-mediated cleavage of mRNA, facilitated by hybridization to antisense ODN, is widely implicated in antisense ODNs action. RNase H, a ubiquitous enzyme found in both nucleus and cytoplasm, can cleave the target RNA at RNA-DNA oligonucleotide duplexes. RNase H cleavage of mRNA thus reflects an important catalytic activity of the antisense ODNs.

Before an ODN exerts its desired effect on gene expression, it must escape nuclease attack in the extracellular medium, cross the cell membrane, escape the attack of intracellular nucleases, and hybridize with the intended target sequence. Modification of the backbone structure of ODNs renders the ODNs resistant to degradation by nucleases and increases their half-life in biological systems. Phosphorothioate oligodeoxynucleotides are far more popular as inhibitors of specific gene expression, are resistant to degradation by RNases, and are potent at nanomolar concentrations. Cells efficiently take them up, apparently via a saturable and energy-dependent process.

Follicle-Stimulating Hormone

It is known that follicle-stimulating hormone ("FSH") is required for the maturation of ovarian follicles and testicular spermatogenesis, and that, in adults, circulating FSH regulates gonadal function and steroidogenesis. FSH regulates folliculogenesis in the ovary and spermatogenesis in the testis via specific, high affinity membrane-bound follicle-stimulating hormone receptors ("FSHR"). FSHR number is determined by the steady state equilibrium between receptor synthesis and receptor degradation.

There are numerous chronic diseases that are a function of altered hormonal status, especially the sex hormones. The most dominant of all of the female hormones are the estrogens which control the reproductive system as well as the function of many other cells and tissues, including bones, as well as the cardiovascular and immune systems, angiogenesis, brain and nerves, and lipid metabolism, etc.

The basic factors controlling female ovarian functions are the anterior pituitary gonadotropins: follicle-stimulating hormone (FSH), which directs follicle and ovum development, and luteinizing hormone (LH) that induces estrogen secretion. The hypothalamus controls the pituitary function by means of secreting pulsatile gonadotropin releasing hormone (GnRH) production. There is a strong negative feedback inhibition of hypothalamus/pituitary function that is conducted by estrogen and inhibin (the latter is a glycoprotein that selectively inhibits FSH secretion).

In puberty the hypothalamic GnRH secretion is raised and this induces estrogen production through pituitary LH. Menarche, the first menstrual period, is delayed for about one to one and one half years, and the early menstrual cycles are usually not accompanied by ovulation, which may be delayed for one to one and one half years. During this overall time of 2 to 3 years there is no established feedback mechanism, either positive or negative. As a result hormonal imbalances are induced and a number of physical and psychological disorders manifest themselves.

Premenstrual tension is exhibited by a series of symptoms that occur during the second, luteal phase of the menstrual cycle. Premenstrual tension is induced by a surge of estrogen that arises because the negative feedback inhibition is altered.

Premenstrual syndrome (PMS) or premenstrual tension is a disorder that affects menstruating women one to two weeks before menses begins. The pathophysiologic mechanisms of PMS are weakly understood. One of the causes is a hormonal imbalance, an excessive estrogen level and an inadequate progesterone level. Estrogen levels in the blood and hypothalamus increase at the end of the first part of the menstrual cycle (the follicular phase); the second peak comes a week before a menstrual flow (the luteal phase). It is the second estrogen peak, which coincides with the progesterone peak, that determines the extent of the PMS.

The clinical diagnosis of PMS involves a combination of physical and behavioral symptoms including headache, breast tenderness, swelling of extremities, tension, anxiety and mood swings. It is possible to differentiate women with three premenstrual symptom severity patterns: premenstrual syndrome (PMS) proper, premenstrual magnification (PMM), and low symptom (LS).

Epithelial Ovarian Cancers

Approximately 24,000 new cases of epithelial ovarian cancer ("EOC") will be diagnosed each year in the United States. Although the absolute number of cases of ovarian cancer pales in comparison to neoplasms of the breast, lung, or colon, ovarian cancer is distinguished by the grim fact that the mortality rate exceeds 70%. Although combination chemotherapy results in disease regression in almost 80% of patients with advanced stage disease, the development of recurrent disease is a common event that ultimately results in death in the majority of cases.

Epithelial ovarian cancer accounts for 80 to 90 percent of ovarian neoplasms. The factors contributing to the initiation, promotion and progression of EOC are incompletely defined. Basic laboratory, animal model and clinical data support the hypothesis that elevated levels of FSH contribute to the pathobiology of this disease. Evidence to support a role for elevated levels of FSH in the promotion and progression of EOC include:

1. The ovarian surface epithelium, which is the origin of epithelial ovarian cancer, expresses the FSH receptor.
2. Proliferation of the ovarian surface epithelial cells can be induced by FSH
3. GnRH agonists inhibit FSH-induced proliferation of ovarian surface epithelial cells
4. Epithelial ovarian cancer primarily occurs in postmenopausal women, in whom serum FSH levels are consistently and chronically elevated
5. Neoplastic epithelial ovarian cells express the FSH receptor
6. Neoplastic epithelial ovarian cells proliferate in response to FSH
7. GnRH agonists inhibit FSH-induce proliferation of neoplastic epithelial ovarian cells
8. The Wx/Wv mouse exhibits spontaneous development of tubular mesothelial adenomas (a precursor lesion of EOC) in response to elevated FSH levels and the development of these precursor lesions can be consistently inhibited by the administration of GnRH agonists
9. In a heterotransplanted model of human ovarian cancer in the nude mouse, tumor growth is significantly greater in surgically castrated animals as compared to age-matched controls.
10. The administration of GnRH agonists to women with advanced stage EOC is occasionally accompanied by a therapeutic response.

Epithelial ovarian cancer develops from the ovarian surface epithelium ("OSE"), which is a single, focally stratified layer of modified peritoneal cells that is separated from the underlying ovarian stroma by a distinct basement membrane. The ovarian surface epithelial cell layer is contiguous with the mesothelial cell layer of the peritoneal cavity but these cell populations can be differentiated on the basis of biochemical and functional differences. Histochemical studies have revealed the presence of glycogen and mucopolysaccharides within the cells that cover the surface of the ovary. These cells weakly express E-cadherin and CA-125.

In addition, cellular membrane receptors are present for estrogen and gonadotropins. Ovarian surface epithelial cells also exhibit 17-beta-hydroxysteroid dehydrogenase activity.

Unlike the peritoneal mesothelium, the epithelial cell layer of the ovary (e.g. the ovarian mesothelium) exhibits a much higher incidence of malignant transformation. Extra-ovarian primary papillary peritoneal carcinoma accounts for only about ten percent of cases presumed to be of ovarian origin based upon intra-operative findings. Although primary ovarian cancer and extra-ovarian papillary peritoneal cancer can be differentiated pathologically, there are few, if any, differences in the epidemiology of these diseases. The proximity of the ovarian mesothelium to the underlying stroma of the ovary provides a unique microenvironment for intercellular interactions. By virtue of this anatomic relationship, the OSE is subject to the effects of steroid hormones and growth factors produced by the ovarian stroma and germ cells of the ovary as well systemic factors, such as elevated levels of FSH.

Epithelial ovarian cancer is generally a disease of postmenopausal women. The incidence of epithelial ovarian cancer ranges from 15.7 per 100,000 women in the 40 to 44 age group to 54 per 100,000 women in the 75 to 79 age group. The mean age at diagnosis is 52 and the disease is uncommon prior to the age of 40. With increasing age, there is a clear increase in the incidence of this disease.

Serum FSH levels are chronically elevated in postmenopausal women, which corresponds to the predominant time of occurrence of EOC. This association has led to the suggestion that elevated gonadotropin levels may play a role in the pathogenesis of this disease. A stimulatory effect of gonadotropins upon the OSE is suggested by the more common occurrence of benign papillary excrescences of the ovarian surface epithelium in postmenopausal as compared to premenopausal women. Additional indirect evidence for a tumorigenic influence of FSH is the observation that patients with gonadal dysgenesis (who have elevated gonadotropin levels) are prone to develop malignant gonadal tumors.

It is well documented that elevated gonadotropin levels are associated with ovarian cancer in most cases, yet serum FSH levels (but not LH) are actually lower in postmenopausal women with ovarian cancer as compared to matched, postmenopausal controls. These data suggest the presence of a tumor-specific inhibitor of FSH release that results in lower serum FSH values in women with ovarian cancer. Inhibin, an ovarian peptide belonging to the TGF beta superfamily, is a potential candidate for this role. Inhibin levels are elevated in some but not all women with advanced stage ovarian cancer. Among epithelial ovarian carcinoma, mucinous cystadenocarcinoma is more likely to be associated with an increased inhibin value than the other histological subtypes.

There is a relationship between serum gonadotropin levels and estrogen replacement therapy (ERT) that merits attention. Women treated with estrogen replacement therapy (ERT) have reduced FSH levels compared to women who do not take ERT. At least one study has suggested that the lifetime risk of EOC is reduced in patients prescribed ERT compared to controls although other studies refute this observation. In one large prospective study of 240,073 peri and postmenopausal women with a seven-year period of follow-up, ever use of estrogen was associated with a rate ratio for fatal ovarian cancer of 1.15 (C10.94-1.42). The risk increased with the duration of estrogen replacement therapy.

Apart from an effect upon serum FSH levels, estrogens also exert a direct effect upon normal and neoplastic OSE cells. Normal OSE cells are estrogen receptor positive. Epithelial ovarian cancers express the estrogen receptor in 70% of cases and the progesterone receptor in 40% of cases. In vitro, 17 beta-estradiol stimulates the proliferation of some but not all estrogen receptor positive cell lines. Estrogens also exert a direct effect upon the ovarian stroma and influence the synthesis of growth factors. Although these observations would suggest that ERT is contraindicated in women with ovarian cancer, there are no published clinical data that suggest that estrogen therapy adversely influences the clinical course of EOC. In fact, ERT may be beneficial by reducing serum gonadotropin levels. It has also been reported that estrogen reduces tumor angiogenesis as well as the invasive potential of neoplastic cells and cell motility in vitro.

Anti-estrogens, such as tamoxifen, inhibit the growth of normal OSE cells as well as the growth in vitro of estrogen receptor positive ovarian cancer cells. However, the anti-proliferative effect of tamoxifen is not restricted exclusively to cells that express the estrogen receptor. Neoplastic OSE cells exhibit tamoxifen binding sites that are distinct from the estrogen receptor and occur in greater numbers than those found on normal OSE cells. In clinical studies, disease stabilization or regression has been reported in approximately 17-18% of women with advanced stage disease treated with tamoxifen as salvage therapy.

The FSH receptor is expressed by OSE and EOC. Gonadotropin receptors for both FSH and LH are present on normal and malignant OSE cells. FSH stimulates the proliferation of FSH-receptor positive cells. When FSH binds to its receptor on a normal OSE cell, proliferation is stimulated. FSH also causes an increase in cell proliferation of some, but not all, ovarian carcinoma cell lines. GnRH agonists decrease the proliferation of FSH receptor positive cells in vitro.

Animal models of epithelial ovarian cancer suggest a role for FSH in ovarian tumorigenesis. The hypothesis that elevated gonadotropins play a role in the promotion of EOC is particularly supported by experiments conducted using the Wx/Wv mouse. The B6C3F1 Wx/Wv strain of mice are born with less than 1% of the normal oocyte complement and exhibit rapid oocyte depletion in early life that is accompanied by a concomitant four fold rise in FSH levels. Accompanying this change is the development of complex tubular mesothelial adenomas in 100% of the animals by 4 to 5 months of age. Tubular mesotheliomas are derived from the ovarian surface epithelium and are considered a precursor lesion of EOC.

When Wx/Wv mice are treated with a GnRH agonist, tubular mesotheliomas do not develop. Blaaker et al (1995) compared tumor development was compared in the control group versus a group of Wx/Wv mice treated with a GnRH agonist (Zoladex). All 15 Wx/Wv mice that received sham injections developed bilateral tubular adenomas from the OSE but none of the 11 GnRH-treated animals developed any tumors (Blaaker J et al. Gonadotropin-releasing hormone agonist suppression of ovarian tumorigenesis in mice of the Wx/Wv genotype. *Biol Reprod* 53:775, 1995).

In a related animal model, mesothelial adenoma formation is also observed when mouse oocytes are destroyed by gamma irradiation early in life. However, mesothelial adenomas do not develop in hypogonadal mice deficient in both GnRH and gonadotropins following gamma irradiation induced oocyte depletion.

Additional data from Peterson et al also indicate that elevated gonadotropin levels appear to play a role in the pathobiology of ovarian cancer. When compared to endocrinologically intact animals, surgically castrated nude mice exhibited significantly greater growth of subcutaneously transplanted human ovarian epithelial carcinoma (BG-1). When surgically castrated nude mice were treated with a long-acting gonadotropin-releasing hormone agonist, the growth of the heterotransplanted tumors was decreased (Peterson C M et al. A long-acting gonadotropin releasing hormone agonist inhibits the growth of a human ovarian epithelial carcinoma (BG-1) heterotransplanted in the nude mouse. *Obstet Gynecol* 76:264, 1990).

A study by Schiffenbauer et al., further supports of a role for FSH in ovarian tumorigenesis (Schiffernbauer Y S, Abramovitch R, Meir G et al. Loss of ovarian function promotes angiogenesis in human ovarian carcinoma. *PNAS* 94:13203-8, 1997). Exogenous gonadotropins stimulated the growth of ovarian carcinoma spheroids implanted in nude mice. Tumor growth was accompanied by neovascularization and elevated serum levels of vascular endothelial growth factor (VEGF). The investigators postulated that elevated gonadotropin levels might facilitate the activation of dormant or subclinical disease. If this were the case, a reduction in serum FSH levels following first line chemotherapy when the patient is clinically free of disease would be of potential therapeutic benefit.

Clinical studies of GnRH agonists have demonstrated a therapeutic effect. Several investigators have reported that reduction in FSH and LH by the administration of LHRH agonists can induce a 20-50% partial remission or stable disease in patients who relapse after failing conventional therapies. Prospective, randomized clinical studies of GnRH agonists in combined with chemotherapy have not confirmed the encouraging observations initially reported in small series and anecdotal case reports. However, the trials, which failed to show a therapeutic benefit from the addition of GnRH agonists, are not truly comparable to the earlier reports in that the patients were earlier in the course of their disease when response rates to chemotherapy are much greater. It is conceivable that any beneficial effect of GnRH agonist therapy was masked by the effect of chemotherapy. In the absence of a prospective, single-agent trial, the issue remains unsettled.

FSH enhances the progression of epithelial ovarian cancers, the predominant form of ovarian cancer. Thus, the compositions of the present invention are useful for blocking FSH action on epithelial ovarian cancer cells, which would limit or prevent the progression of the disease. The FSHR antisense oligodeoxynucleotides of the present invention can specifically block FSH action because it has been shown to inhibit synthesis of the FSH receptor. It would have no effect on any cell that does not have FSH receptor. Preferably, the antisense compounds are administered in a sustained release depot formulation as a chemopreventive or as a chemotherapeutic for various cancers, especially ovarian cancers.

BRIEF SUMMARY OF THE INVENTION

Figure 1:
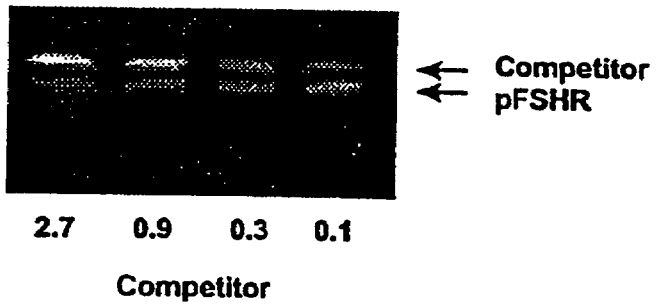
FIG. 1 Reverse transcription and competitive polymerase chain reaction. Total RNA was extracted and transcribed. Fixed amount of RT products and different concentrations of competitive template were co-amplified using the same external primers. Ethidium bromide-stained gel showed bands corresponding to the competitive template and the pFSHR cDNA FIG. 2 Effect of ODNs on pFSHR mRNA expression in 24 h. Cells were cultured with 0-20 μM either antisense ODN or nonsense ODN for 24 h. Total RNA was extracted and pFSHR mRNA content was quantitated by reverse transcription and competitive polymerase chain reaction.

The present invention provides compositions and methods for fertility regulation. In one aspect, the present invention consists of a phosphorothioated 18-mer antisense oligodeoxynucleotide ("[S] ODN") that is complementary to the nucleotide sequence around initiation codon (ATG) of the follicle-stimulating hormone receptor ("FSHR") messenger ribonucleic acid ("mRNA").

The advantage of using the antisense ODN for inhibiting FSH receptor synthesis and, thus ovarian follicular development, is the high degree of specificity. The antisense compounds of the present invention will only bind to the FSHR mRNA which, to the best of our current knowledge, is synthesized only in ovarian follicular granulosa cells. That means that a contraceptive based on the FSHR antisense ODN would not affect any other cells in the body, unlike estrogens and progestins, which affect the brain, skeleton, liver, kidneys, heart, etc. The present methods and compounds should then have no other effects in the body.

According to the present invention, a composition is provided comprising at least one antisense oligonucleotide specific for FSHR.

According to one embodiment, the oligonucleotide has a nucleotide sequence capable of forming a stable duplex with a portion of an mRNA transcript of the FSHR gene.

DETAILED DESCRIPTION OF THE INVENTION

Definitions

By "protein tyrosine kinase" is meant an enzyme that catalyzes the transfer of a phosphate residue form a nucleoside triphosphate to the side chain of a tyrosine amino acid residue in a protein.

By "transcriptional factor" is meant the product of a gene that binds a target DNA segment to activate transcription of another gene.

An "antisense oligonucleotide specific for FSHR" means an oligonucleotide having a sequence (i) capable of forming a stable triplex with a portion of the FSHR gene, or (ii) capable of forming a stable duplex with a portion of an mRNA transcript of the FSHR gene.

The term "oligonucleotide" as used herein includes linear oligomers of natural or modified monomers or linkages, including deoxyribonucleosides, ribonucleosides, alpha-anomeric forms thereof, polyamide nucleic acids, and the like, capable of specifically binding to a target polynucleotide by way of a regular pattern of monomer-to-monomer interactions, such as Watson-Crick type of base pairing, Hoogsteen or reverse Hoogsteen types of base pairing, or the like. Usually, monomers are linked by phosphodiester bonds or analogs thereof to form oligonucleotides ranging in size from a few monomeric units, e.g., 3-4, to several hundreds of monomeric units. Analogs of phosphodiester linkages include phosphorothioate, phosphorodithioate, phosphoroselenoate, phosphorodiselenoate, phosphoroanilothioate, phosphoranilidate, phosphoramidate, and the like, as more fully described below. As used herein, "nucleotide" and "nucleoside" includes the natural nucleotides and nucleosides, including 2'-deoxy and 2'-hydroxyl forms, e.g., as described in Kornberg and Baker, DNA Replication, 2nd Ed. (Freeman, San Francisco, 1992). "Analogs" in reference to nucleosides includes synthetic nucleotides having modified base moieties and/or modified sugar moieties, e.g., described generally by Scheit, Nucleotide Analogs (John Wiley, New York, 1980). Such analogs include synthetic nucleotides designed to enhance binding properties, e.g., duplex or triplex stability, specificity, or the like.

The term "phosphorothioate oligonucleotide" means an oligonucleotide wherein one or more of the internucleotide linkages is a phosphorothioate group, as opposed to the phosphodiester group which is characteristic of unmodified oligonucleotides.

By "alkylphosphonate oligonucleoside" is meant an oligonucleotide wherein one or more of the internucleotide linkages is an alkylphosphonate group.

The term "modified oligonucleotide" is meant an oligonucleotide containing one or more modified monomers and/or linkages to enhance the stability or uptake of the oligonucleotide.

"Stability" in reference to duplex or triplex formation roughly means how tightly an antisense oligonucleotide binds to its intended target sequence; more precisely, it means the free energy of formation of the duplex or triplex under physiological conditions. Melting temperature under a standard set of conditions, e.g., as described below, is a convenient measure of duplex and/or triplex stability. Preferably, antisense oligonucleotides of the invention are selected that have melting temperatures of at least 50° C. under the standard conditions set forth below; thus, under physiological conditions and the preferred concentrations, duplex or triplex formation will be substantially favored over the state in which the antisense oligonucleotide and its target are dissociated. It is understood that a stable duplex or triplex may in some embodiments include mismatches between base pairs and/or among base triplets in the case of triplexes. Preferably, antisense oligonucleotides of the invention form perfectly matched duplexes and/or triplexes with their target polynucleotides.

The term "downstream" when used in reference to a direction along a nucleotide sequence means the 5'→3' direction. Similarly, the term "upstream" means the 3'→5' direction.

The term "targeted gene mRNA transcript" means the presently known mRNA transcript of the targeted gene and all variations thereof, or any further transcripts which may be elucidated.

The term "[S]-ODN" means phosphorothioate oligonucleotide.

A cell line is said to be "malignant" if, when the cell line is injected into a host animal, the host animal develops tumors or cancers that are anaplastic, invasive, and/or metastatic. A "human" tumor is comprised of cells that have human chromosomes. Such tumors include those in a human patient, and tumors resulting from the introduction of a human malignant cell line into a non-human host animal if cells from such tumors have human chromosomes. A tumor is said to be "long-lasting" when the tumor persists in an animal for at least about one month.

The term "effective amount" means a dosage sufficient to produce a desired result. The desired result in treatment of tumors, including cancers, can be subjective or objective improvement in the recipient of the dosage, a decrease in tumor size, a decrease in the rate of growth of cancer cells, or a decrease in metastasis.

The terms "treating cancer", "therapy", and the like mean generally a treatment that causes any improvement in a mammal having a cancer wherein the improvement can be ascribed to treatment with the ODN. The improvement can be either subjective or objective. For example, if the mammal is human, the patient may note improved vigor or vitality or decreased pain as subjective symptoms of improvement or response to therapy. Alternatively, the clinician may notice a decrease in tumor size or tumor burden based on physical exam, laboratory parameters, tumor markers, or radiographic findings.

Some laboratory signs that the clinician may observe for response to therapy include normalization of tests such as white blood cell count, red blood cell count, platelet count, erythrocyte sedimentation rate, and various enzyme levels such as transaminases and hydrogenases. Additionally, the clinician may observe a decrease in a detectable tumor marker such as prostatic specific antigen (PSA) or chorio embryonic antigen (CEA). Alternatively, other tests can be used to evaluate objective improvement such as sonongrams, nuclear magnetic resonance testing and positron emissions testing.

"Inhibiting the growth of cancer cells" can be evaluated by any accepted method of measuring whether growth of the cancer cells has been slowed or diminished. This includes direct observation and indirect evaluation such as subjective symptoms or objective signs as discussed above.

An "antisense ODN-responsive tumor" refers to a tumor or cancer that responds to treatment with an antisense ODN that is complementary to the nucleotide sequence around initiation codon (ATG) of the targeted gene messenger ribonucleic acid ("mRNA") transcript. Preferably, the targeted gene mRNA transcript is for the mRNA of follicle-stimulating hormone receptor ("FSHR"), luteinizing hormone receptor ("LHR"), human chorionic gonadotropin receptor ("hCGR"), platelet-derived growth hormone receptor ("PDGF-R"), or a biologically active subfragment. To determine whether a cancer is antisense ODN-responsive, the clinician can test whether antisense ODN treatment inhibits growth of cells derived from a cancer of that particular type. Appropriate assays are well known in the art.

A "biologically active fragment" of an antisense ODN is one that exhibits a biological activity in a patient. To determine whether an antisense ODN fragment is biologically active, one can perform an assay to detect a biological effect that is typical of cells. Alternatively, one can test the fragment to determine whether it binds to the appropriate targeted gene mRNA transcript.

The present invention provides compositions and methods for fertility regulation. In one aspect, the present invention consists of a phosphorothioated 18-mer antisense oligodeoxynucleotide ("[S] ODN") that is complementary to the nucleotide sequence around the initiation codon (AUG) of the targeted gene mRNA transcript. Preferably, this is complementary to follicle-stimulating hormone receptor ("FSHR") messenger ribonucleic acid ("mRNA").

The antisense ODN works by being taken up by living cells where it then binds to the targeted gene mRNA transcript, e.g., the messenger ribonucleic acid encoding the FSHR. It binds only to the mRNA encoding the FSHR because it is sequence-specific and will bind only to the complementary sequence. Binding of the antisense ODN to the mRNA prevents translation of targeted gene protein and hastens degradation of the mRNA itself. This leads to a loss of the targeted gene receptor protein from the cell surface. In a preferred embodiment, in the only cell that is presently known to express FSHR, a normal ovarian granulosa cell, the inhibition of FSHR synthesis causes a failure of ovarian follicles to develop with a resulting degradation of ovarian follicles. This effectively prevents ovulation and pregnancy and results in contraception.

The effectiveness of the ODN is determined by the ability of the ODN to be taken up by living cells and the ability of the ODN to bind to the targeted gene mRNA transcript, e.g., FSHR mRNA. Oligodeoxynucleotides with a different sequence would be equally effective is if they were able to bind the mRNA.

The advantage of using the antisense ODN for inhibiting FSH receptor synthesis and, thus ovarian follicular development, is the high degree of specificity. The antisense compounds of the present invention will only bind to the FSHR mRNA that is synthesized only in ovarian follicular granulosa cells. That means that a contraceptive based on the FSHR antisense ODN would not affect any other cells in the body, unlike estrogens and progestins, which affect the brain, skeleton, liver, kidneys, heart, etc. the present methods and compounds should then have no other effects in the body.

According to the present invention, a composition is provided comprising at least one antisense oligonucleotide specific for a polypeptide hormone receptor mRNA. Preferably, the antisense oligonucleotide is specific for the receptor mRNA of FSH, LH or hCG. More preferably, the antisense oligonucleotide is specific for the mRNA of the FSHR gene.

According to one embodiment, the oligonucleotide has a nucleotide sequence capable of forming a stable duplex with a portion of an mRNA transcript of the FSHR gene.

Each antisense oligonucleotide specific for an mRNA transcript of a polypeptide hormone receptor gene is generally at least an 8-mer oligonucleotide; that is, the oligonucleotide is an oligomer containing at least 8 nucleotide residues, more preferably at least about 12 nucleotides. The preferred maximum size of the oligonucleotide is about 60 nucleotides, more preferably about 50 nucleotides, most preferably about 40 nucleotides. The oligomer is preferably an oligodeoxynucleotide. While oligonucleotides smaller than 12-mers may be utilized, they are statistically more likely to hybridize with non-targeted sequences, and for this reason may be less specific. In addition, a single mismatch may destabilize the hybrid. While oligonucleotides larger than 40-mers may be utilized, uptake may become somewhat more difficult without specialized vehicles or oligonucleotide carriers. Moreover, partial matching of long sequences may lead to non-specific hybridization, and non-specific effects. Most preferably, the oligonucleotide is a 15- to 40-mer oligodeoxynucleotide, more advantageously an 18- to 30-mer.

While in principle oligonucleotides having a sequence complementary to any region of the target mRNA find utility in the present invention, preferred are oligonucleotides capable of forming a stable duplex with a portion of the transcript lying within about 50 nucleotides (preferably within about 40 nucleotides) upstream (the 5' direction), or about 50 (preferably 40) nucleotides downstream (the 3' direction) from the translation initiation codon of the target mRNA. Also preferred are oligonucleotides which are capable of forming a stable duplex with a portion of the target mRNA transcript including the translation initiation codon.

The invention is also a method for inhibiting fertility in a mammal host comprising contacting host ovarian cells with an FSHR inhibiting effective amount of at least one antisense oligonucleotide specific for FSHR.

The invention also provides a method for preventing estrogen synthesis, a function of developing ovarian follicles, a therapeutic consideration for the prevention and treatment of some cancers of the breast, endometrium, ovary and cervix and of some endometriosis comprising administering to a patient in need of such treatment an effective amount of at least one antisense oligonucleotide specific for FSHR.

Methods are disclosed for regulating ovulation or fertility in female mammals, for regulating spermatogenesis in males and for treating conditions such as endometriosis, and tumors, including cancers. Administration of effective amounts of one or more antisense oligonucleotides to receptor FSHR genes that can be used for female contraception and also for male contraception by preventing sperm production.

The invention is also a method and formulation useful for menstrual cycle regulation to achieve ovulation control and to treat menstrual dysfunction. More particularly, the present invention provides antisense oligonucleotides to receptor genes that may be adapted to the specific presenting clinical state of the individual patent. Thus, the methods of the present invention are useful in the management of clinical states of menstrual irregularity, menstrual dysfunction, ovulation pain, primary dysmenorrhea, premenstrual tension syndrome, and menopausal dysfunction.

The invention also provides methods for treating tumors, including cancers, in a patient. The methods involve administering to the patient a therapeutically effective amount of a pharmaceutical agent containing one or more antisense oligonucleotides to receptor genes, e.g., the genes encoding the receptors for LH, FSH, and hCG. More preferably, the methods involve administering to the patient a therapeutically effective amount of a pharmaceutical agent containing one or more antisense oligonucleotide specific for the mRNA of the FSHR gene.

Specifically, the compositions and methods of the present invention are useful in treatment of a gestational trophoblastic tumor, a testicular germ cell tumor, or a cancer of the breast, bladder, pancreas, cervix, lung, liver, ovary, colon, or stomach. Typically the cancer is a sarcoma, carcinoma, or neuroblastoma. The present invention is particularly useful in treating a carcinoma such as those of breast, prostate, ovary, and stomach carcinomas.

According to one method of the present invention, at least one antisense oligonucleotide specific for the targeted gene mRNA transcript is administered to a patient in a safe and effective amount.

According to one preferred embodiment of the invention, the therapeutic combination comprises one or more antisense oligonucleotides specific for FSHR gene in the ovarian granulosa cell of a human host.

The following nucleotide sequences are set forth herein:

human

5'-GAGCAGGGCCATAATTAT-3'    SEQ ID NO:1

5'-AUAAUUAUGGCCCUGCUC-3'    SEQ ID NO:2 porcine

5'-GAGCAAGGACATGATTAT-3'    SEQ ID NO:3

5'-AUAAUGAUGUCCUUGCUC-3'    SEQ ID NO:4

An antisense oligonucleotide according to the invention may have differing lengths. Lengths of 20 to 30 nucleotides are preferred. Furthermore, the antisense oligonucleotide may have variations in its sugar and phosphate components each. The sugar component conceivable is deoxyribose, ribose or a chemical variant thereof, for example. The phosphate component may be, e.g., ortho-phosphoric acid diester or a chemical variant thereof. A preferred antisense oligonucleotide contains deoxyribose as sugar component and ortho-phosphoric acid diester as phosphate component.

The sequence of an antisense oligonucleotide according to the invention may be fully complementary to the DNA and/or mRNA sequence to be bonded. On the other hand, the antisense oligonucleotide may also contain one or more nucleotides which are not complementary to the corresponding nucleotides of the sequence to be bonded.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases. Particularly preferred are antisense oligonucleotides comprising from about 8 to about 30 nucleobases (i.e. from about 8 to about 30 linked nucleosides). As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference.

Most preferred embodiments of the invention are oligonucleotides with phosphorothioate backbones and oligonucleosides with heteroatom backbones, and in particular —CH2-NH—O—CH2-, —CH2-N(CH3)—O—CH2- [known as a methylene (methylimino) or MMI backbone], —CH2-O—N(CH3)—CH2-, —CH2-N(CH3)—N(CH3)—CH2- and —O—N(CH3)—CH2-CH2- [wherein the native phosphodiester backbone is represented as —O—P—O—CH2-] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O-, S-, or N-alkyl; O-, S-, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Particularly preferred are O[(CH2)[n]O][m]CH3, O(CH2)[n]OCH3, O(CH2)[n]NH2, O(CH2)[n]CH3, O(CH2)[n]ONH2, and O(CH2)[n]ON [(CH2)[n]CH3)]2 where n and m are from 1 to about 10. Other preferred oligonucleotides comprise one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2CH2OCH3, also known as 2'-O-(2-methoxyethyl) or 2'-MOE) (Martin et al., Helv. Chim. Acta, 1995, 78, 486-504) i.e., an alkoxyalkoxy group. A further preferred modification includes 2'-dimethylaminooxyethoxy, i.e., a O(CH2)2ON(CH3)2 group, also known as 2'-DMAOE, as described in examples hereinbelow.

Other preferred modifications include 2'-methoxy (2'-O—CH3), 2'-aminopropoxy (2'-OCH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference in its entirety.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N. Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007;

5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The antisense compounds of the invention are synthesized in vitro and do not include antisense compositions of biological origin, or genetic vector constructs designed to direct the in vivo synthesis of antisense molecules. The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 to Imbach et al.

Antisense compounds of the invention may also contain pendent groups, moieties, or modifications, either as part of or separate from the basic repeat unit of the polymer, to enhance specificity, nuclease resistance, delivery, or other property related to efficacy, e.g., cholesterol moieties, duplex intercalators such as acridine, poly-L-lysine, phosphorothioate derivatives, and the like.

For example, it is known that enhanced lipid solubility and/or resistance to nuclease digestion results by substituting an alkyl group or alkoxy group for a phosphate oxygen in the internucleotide phosphodiester linkage to form an alkylphosphonate oligonucleoside or alkylphosphotriester oligonucleotide. Non-ionic oligonucleotides such as these are characterized by increased resistance to nuclease hydrolysis and/or increased cellular uptake, while retaining the ability to form stable complexes with complementary nucleic acid sequences. The alkylphosphonates, in particular, are stable to nuclease cleavage and soluble in lipid. The preparation of alkylphosphonate oligonucleosides is disclosed in Tso et al., U.S. Pat. No. 4,469,863, incorporated herein in its entirety.

Preferably, nuclease resistance is conferred on the antisense compounds of the invention by providing nuclease-resistant internucleosidic linkages. Many such linkages are known in the art, e.g., phosphorothioate; phosphorodithioates; phosphoramidates; peptide nucleic acids; methylphosphonates; and P-chiral linkages of various types, especially phosphorothioates. Additional nuclease linkages include phosphoroselenoate, phosphorodiselenoate, phosphoroanilothioate, phosphoranilidate, alkylphosphotriester such as methyl- and ethylphosphotriester, carbonate such as carboxymethyl ester, carbamate, morpholino carbamate, 3'-thioformacetal, silyl such as dialkyl (C1-C6)— or diphenylsilyl, sulfamate ester, and the like. Such linkages and methods for introducing them into oligonucleotides are described in many references, e.g., Milligan et al., J. Med. Chem., 36:1923-1937 (1993).

Resistance to nuclease digestion may also be achieved by modifying the internucleotide linkage at both the 5' and 3' termini with phosphoroamidites according to the procedure of Dagle et al., Nucl. Acids Res. 18, 4751-4757 (1990).

Preferably, phosphorus analogs of the phosphodiester linkage are employed in the compounds of the invention, such as phosphorothioate, phosphorodithioate, phosphoramidate, or methylphosphonate. More preferably, phosphorothioate is employed as the nuclease resistant linkage.

Phosphorothioate oligonucleotides contain a sulfur-for-oxygen substitution in the internucleotide phosphodiester bond. Phosphorothioate oligonucleotides combine the properties of effective hybridization for duplex formation with substantial nuclease resistance, while retaining the water solubility of a charged phosphate analogue. The charge is believed to confer the property of cellular uptake via a receptor (Loke et al., Proc. Natl. Acad. Sci., 86, 3474-3478 (1989)).

It is understood that in addition to the preferred linkage groups, compounds of the invention may comprise additional modifications, e.g., boronated bases, cholesterol, and 5-propynyl modification of pyrimidines.

Preferably, antisense compounds of the invention are synthesized by conventional means on commercially available automated DNA synthesizers. Preferably, phosphoramidite chemistry is employed, e.g., U.S. Pat. Nos. 4,415,732; 4,458,066; and 4,973,679, herein incorporated in their entirety by reference.

In general, the antisense oligonucleotides used in the practice of the present invention will have a sequence that is completely complementary to a selected portion of the target polynucleotide. Absolute complementarity is not however required, particularly in larger oligomers. Thus, reference herein to a "nucleotide sequence complementary to" a target polynucleotide does not necessarily mean a sequence having 100% complementarity with the target segment. In general, any oligonucleotide having sufficient complementarity to form a stable duplex with the target (e.g. a messenger RNA) that is, an oligonucleotide which is "hybridizable", is suitable. Stable duplex formation depends on the sequence and length of the hybridizing oligonucleotide and the degree of complementarity with the target polynucleotide. Generally, the larger the hybridizing oligomer, the more mismatches may be tolerated. More than one mismatch probably will not be tolerated for antisense oligomers of less than about 21 nucleotides. One skilled in the art may readily determine the degree of mismatching which may be tolerated between any given antisense oligomer and the target sequence, based upon the melting point, and therefore the thermal stability, of the resulting duplex.

Preferably, the thermal stability of hybrids formed by the antisense oligonucleotides of the invention are determined by way of melting, or strand dissociation, curves. The temperature of fifty-percent strand dissociation is taken as the melting temperature, T[m], which, in turn, provides a convenient measure of stability. T[m] measurements are typically carried out in a saline solution at neutral pH with target and antisense oligonucleotide concentrations at between about 1.0-2.0 µM. Typical conditions are as follows: 150 mM NaCl and 10 mM $MgCl_2$ in a 10 mM sodium phosphate buffer (pH 7.0) or in a 10 mM Tris-HCl buffer (pH 7.0). Data for melting curves are accumulated by heating a sample of the antisense oligonucleotide/target polynucleotide complex from room temperature to about 85° C. As the temperature of the sample increases, absorbance of 260 nm light is monitored at 1° C. intervals, e.g., using a Cary (Australia) model 1E or a Hewlett-Packard (Palo Alto, Calif.) model HP 8459 UV/VIS spectrophotometer and model HP 89100A temperature controller, or like instruments. Such techniques provide a convenient means for measuring and comparing the binding strengths of antisense oligonucleotides of different lengths and compositions.

Pharmaceutical compositions of the invention include a pharmaceutical carrier that may contain a variety of components that provide a variety of functions, including regulation of drug concentration, regulation of solubility, chemical stabilization, regulation of viscosity, absorption enhancement, regulation of pH, and the like. The pharmaceutical carrier may comprise a suitable liquid vehicle or excipient and an optional auxiliary additive or additives. The liquid vehicles and excipients are conventional and commercially available. Illustrative thereof are distilled water, physiological saline, aqueous solutions of dextrose, and the like. For water-soluble formulations, the pharmaceutical composition preferably includes a buffer such as a phosphate buffer, or other organic acid salt, preferably at a pH of between about 7 and 8. For formulations containing weakly soluble antisense compounds, micro-emulsions may be employed, for example, by using a nonionic surfactant such as polysorbate 80 in an amount of 0.04-0.05% (w/v), to increase solubility. Other components may include antioxidants, such as ascorbic acid, hydrophilic polymers, such as, monosaccharides, disaccharides, and other carbohydrates including cellulose or its derivatives, dextrins, chelating agents, such as EDTA, and like components well known to those in the pharmaceutical sciences.

Antisense compounds of the invention include the pharmaceutically acceptable salts thereof, including those of alkaline earths, e.g., sodium or magnesium, ammonium or $NX_4^+$, wherein X is C1-C4 alkyl. Other pharmaceutically acceptable salts include organic carboxylic acids such as acetic, lactic, tartaric, malic, isethionic, lactobionic, and succinic acids; organic sulfonic acids such as methanesulfonic, ethanesulfonic, and benzenesulfonic; and inorganic acids such as hydrochloric, sulfuric, phosphoric, and sulfamic acids. Pharmaceutically acceptable salts of a compound having a hydroxyl group include the anion of such compound in with a suitable cation such as $Na^+$, $NH_4^+$, or the like.

It is contemplated that such target cells may be located within an animal or human patient, in which case a safe and effective amount of the complex, in pharmacologically acceptable form, would be administered to the patient. Generally speaking, it is contemplated that useful pharmaceutical compositions of the present invention will include the selected ODNs in a convenient amount, e.g., from about 0.001% to about 90% (w/w) that is diluted in a pharmacologically or physiologically acceptable carrier, such as, for example, phosphate buffered saline. The route of administration and ultimate amount of material that is administered to the patient or animal under such circumstances will depend upon the intended application and will be apparent to those of skill in the art in light of the examples which follow.

The compound useful in the present inventive method may be administered by any suitable means. One skilled in the art will appreciate that many suitable methods of administering the compound to a host in the context of the present invention, in particular a human, are available, and, although more than one route may be used to administer a particular compound, a particular route of administration may provide a more immediate and more effective reaction than another route.

Formulations suitable for administration by inhalation include aerosol formulations placed into pressurized acceptable propellants, such as dichlorodifluoromethane, propane, nitrogen, and the like. The active agent may be aerosolized with suitable excipients. For inhalation administration, the composition can be dissolved or dispersed in liquid form, such as in water or saline, preferably at a concentration at which the composition is fully solubilized and at which a suitable dose can be administered within an inhalable volume. A suitable dose would place approximately 0.001 to about 5.0 mmol per liter of the composition on the airway surfaces approximately 4 times per day. Delivery can be repeated several times a day, depending upon the specific dosage chosen and the rate at which the chosen composition is cleared from the airways, with the goal being to maintain fertility in the host.

Formulations suitable for oral administration include (a) liquid solutions, such as an effective amount of the compound dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms may include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels and the like containing, in addition to the active ingredient, such carriers as are known in the art.

Formulations suitable for intravenous and intraperitoneal administration, for example, include aqueous and nonaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carriers for example, water, for injections, immediately prior to use. Extemporaneous injection solutions and suspensions can be prepared for sterile powders, granules, and tablets of the kind previously described.

Parenteral administration, if used, could also be by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795, Higuchi, issued 1973, which is incorporated by reference herein.

Powders, dispersible powders or granules suitable for preparation of an aqueous suspension by addition of water are also convenient dosage forms of the present invention. Formulation as a suspension provides the active ingredient in admixture with a dispersing or wetting agent, suspending agent and one or more preservatives. Suitable dispersing or wetting agents are, for example, naturally-occurring phosphatides, as e.g. lecithin, or condensation products of ethylene oxide with e.g. a fatty acid, a long chain aliphatic alcohol or a partial ester derived from fatty acids and a hexitol or a hexitol anhydrides, for example, polyoxyethylene stearate, polyoxyethylene sorbitol monooleate, polyoxyethylene sorbitan monooleate etc. Suitable suspending agents are, for example, sodium carboxymethylcellulose, methylcellulose, sodium alginate etc.

In addition to administration with conventional carriers, the antisense oligonucleotides may be administered by a variety of specialized oligonucleotide delivery techniques. Sustained release systems suitable for use with the pharmaceutical compositions of the invention include semi-permeable polymer matrices in the form of films, microcapsules, or the like, comprising polylactides; copolymers of L-glutamic acid and gamma-ethyl-L-glutamate, poly(2-hydroxyethyl methacrylate), and like materials, e.g., Rosenberg et al., International application PCT/US92/05305.

The oligonucleotides may be encapsulated in liposomes for therapeutic delivery, as described for example in Liposome Technology, Vol. II, Incorporation of Drugs, Proteins, and Genetic Material, CRC Press. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature.

The oligonucleotides may be conjugated to poly(L-lysine) to increase cell penetration. Such conjugates are described by Lemaitre et al., Proc. Natl. Acad. Sci. USA, 84, 648-652 (1987). The procedure requires that the 3'-terminal nucleotide be a ribonucleotide. The resulting aldehyde groups are then randomly coupled to the epsilon-amino groups of lysine residues of poly(L-lysine) by Schiff base formation, and then reduced with sodium cyanoborohydride. This procedure converts the 3'-terminal ribose ring into a morpholine structure antisense oligomers.

Antisense compounds of the invention also include conjugates of such oligonucleotides with appropriate ligand-binding molecules. The oligonucleotides may be conjugated for therapeutic administration to ligand-binding molecules that recognize cell-surface molecules. The ligand-binding molecule may comprise, for example, an antibody against a cell surface antigen, an antibody against a cell surface receptor, a growth factor having a corresponding cell surface receptor, an antibody to such a growth factor, or an antibody which recognizes a complex of a growth factor and its receptor.

Examples of emulsifying agents are naturally occurring gums, e.g., gum acacia or gum tragacanth, naturally occurring phosphatides, e.g., soybean lecithin and sorbitan monooleate derivatives.

Examples of antioxidants are butylated hydroxy anisole (BHA), ascorbic acid and derivatives thereof, tocopherol and derivatives thereof and cysteine.

Examples of preservatives are parabens and benzalkonium chloride.

Examples of humectants are glycerin, propylene glycol, sorbitol and urea.

Examples of penetration enhancers are propylene glycol, DMSO, triethanoiamine, N,N-dimethylacetamide, N,N-dimethylformamide, 2-pyrrolidone and derivatives thereof, tetrahydrofurfuryl alcohol and AZONE®.

Examples of chelating agents are sodium EDTA, citric acid and phosphoric acid.

Examples of gel forming agents are Carbopol, cellulose derivatives, bentonite, alginates, gelatin and PVP.

The formulation and preparation of the above-mentioned compositions is well known to those skilled in the art of pharmaceutical formulation. Specific formulation can be found in "Remington's Pharmaceutical Sciences" incorporated herein by reference.

The compound should be administered such that a therapeutically effective concentration of the compound is in contact with the affected cells of the host. The dose administered to an animal, particularly a human, in the context of the present invention should be sufficient to effect a therapeutic response in the animal over a reasonable period of time. The dose will be determined by the strength of the particular compound employed and the condition of the animal, as well as the body weight of the animal to be treated. The existence, nature, and extent of any adverse side effects that might accompany the administration of a particular compound also will determine the size of the dose and the particular route of administration employed with a particular patient. In general, the compounds of the present invention are therapeutically effective at low doses. The effective dose range is from about 0.01 mM to about 10 mM. Accordingly, the compounds will be generally administered in low doses.

As used herein, "an effective amount" of a composition is that amount of an oligonucleotide capable of binding with a portion of an mRNA transcript of the FSHR gene and inhibits translation of FSHR protein leading to a failure of ovarian follicles to develop. As used herein, "a safe and effective amount" of a composition is that amount which is pharmaceutically safe to a subject and that inhibits the translation of FSHR protein leading to a failure of ovarian follicles to develop and effectively preventing ovulation and contraception while causing no side effects or an acceptable level of side effects.

The exact amount of such compounds required will vary from subject to subject, depending on the species, age, and general condition of the subject, the severity of the disease that is being treated, the particular compound used, its mode of administration, and the like. Thus, it is not possible to specify an exact activity-promoting amount. However, an appropriate amount may be determined by one of ordinary skill in the art using only routine testing given the teachings herein.

The antisense oligonucleotides may be used as the primary therapeutic for the treatment of the disease state, or may be used in with non-oligonucleotide agents. In particular, the antisense oligonucleotides may find utility as fertility and menstrual cycle regulating agents in combination with one or more known fertility-regulating agent. Preferably, for fertility and menstrual cycle regulation, the antisense oligonucleotides are used in combination with one or more agents such as estrogenic steroids or progestogens to prevent hypoestrogenic or hypoprogestogenic symptoms.

The preferred estrogenic steroid is estradiol, estradiol benzoate, estradiol cypionate, estradiol valerate, estrone, diethylstilbestrol, piperazine estrone sulfate, ethinyl estradiol, mestranol, polyestradiol phosphate, estriol, estriol hemisuccinate, quinestrol, estropipate, pinestrol, estrone potassium sulfate, equilelinin, equilelinin sulfate, estetrol and mixtures of two or more thereof.

The preferred progestogen is progesterone, ethynodiol diacetate, hydroxyprogesterone caproate, medroxyprogesterone acetate, norethindrone, norethindrone acetate, norethynodrel, norgestrel, progesterone, megestrol acetate and mixtures of two or more thereof.

Breast or ovarian cancer be treated by the administration of a therapeutically effective amount of the antisense oligonucleotides via an efficient method, such as injection into a tumor. A therapeutically effective amount can be determined by one having ordinary skill in the art using well-known protocols.

Antisense oligonucleotides may be used a chemopreventive agent by introducing antisense oligonucleotides directly into the peritoneal cavity of women as the whole protein, as a functional fragment, or as a functional cleavage product. The protective effect is also expected where antisense oligonucleotides expression is mediated by gene therapy method by either directly or indirectly inducing expression of antisense oligonucleotides.

The appropriate dosage administered in any given case will, of course, vary depending upon known factors, such as the pharmacodynamic characteristics of the particular agent and its mode and route of administration; the age, general health, metabolism, weight of the recipient and other factors which influence response to the compound; the nature and extent of the symptoms; the kind of concurrent treatment; the frequency of treatment; and the effect desired. A daily dosage of active ingredient can be expected to be about 0.5-10,000 mg/m$^2$ body mass for the antisense oligonucleotide.

Dosage forms (compositions suitable for administration) contain from about 0.1 mg to about 10 g of active ingredient per unit. In these pharmaceutical compositions the active ingredient(s) will ordinarily be present in an amount of about 0.5-95% by weight based on the total weight of the composition.

Treatment for advanced ovarian cancer generally includes cytoreductive surgery followed by combination chemotherapy. In particular, the antisense oligonucleotides may find utility as chemotherapy or chemopreventative agents in combination with one or more known chemotherapy or chemopreventative agent. Antisense oligonucleotide compounds may be used in combination with a variety of chemotherapeutic drugs that produce a desired therapeutic effect by interfering with a variety of cellular processes. The compositions of the present invention are useful in preventing the transformation of preneoplastic cells to tumor cells, and inhibiting tumor cell proliferation, invasion and metastasis.

The "pharmaceutical agents" for use in the methods of the invention include, but are not limited to, antisense compounds that act as anticancer agents as well as differentiating agents. Further, the pharmaceutical agent can include one or more compounds such as a cytokine, an interleukin, an anti-cancer agent, a chemotherapeutic agent, an antibody, a conjugated antibody, an immune stimulant, an antibiotic, a hormone antagonist or a growth stimulant.

As used herein, the "chemotherapeutic agents" include but are not limited to alkylating agents, purine and pyrimidine analogs, vinca and vinca-like alkaloids, etoposide and etoposide-like drugs, corticosteroids, nitrosoureas, antimetabolites, platinum-based cytotoxic drugs, hormonal antagonists, anti-androgens and antiestrogens.

The "cytokines" for use herein include but are not limited to interferon, preferably alpha, beta or gamma interferon, as well as IL-2, IL-3, G-CSF, GM-CSF and EPO.

As used herein, an "immune stimulant" is a substance such as C. parvum or sarcolectin which stimulates a humoral or cellular component of the immune system.

The "chemotherapeutic agents" of the invention include but are not limited to tamoxifen, doxorubicin, L-asparaginase, dacarbazine, amsacrine, procarbazine, hexamethylmelamine, mitoxantrone and gemcitabine.

The commonly used chemotherapeutic agents which can be employed with the antisense oligonucleotides according to the present invention include a variety of agents which are classified by their mode of action, origin or structure, although some drugs do not fit clearly into any single group. The categories include alkylating agents, antimetabolites, antibiotics, alkaloids and miscellaneous agents including hormones.

Alkylating agents (e.g., nitrogen mustard, cyclophosphamide, melphalan, busulfan, etc.) form covalent bonds with nucleic acids. These agents alter the integrity of DNA by transferring an alkyl group to the nucleic acids. Agents in this class have toxicities related to bone marrow depression, amenorrhea, male sterility, etc.

Antimetabolites (e.g., methotrexate, mercaptopurine, thioguanine, fluorouracil, etc.) are structurally similar to normal metabolic substrates. They impair cellular functions by substituting for normal precursors in vital physiologic reactions or by blocking these reactions. Agents in this class have toxicities related to bone marrow depression, liver damage, etc.

Antibiotics (e.g., doxorubicin, daunorubicin, bleomycin, etc.) are biologic products of bacteria and fungi. They do not share a single mechanism of action. For example, the anthracyclines, doxorubicin and daunorubicin achieve their cytotoxic effect by several mechanisms, including intercalation between DNA strands, production of free radicals, chelation of divalent cations and reaction with cell membranes. The wide range of potential sites of action may account for the broad efficacy as well as the toxicity of the anthracyclines.

Alkaloids (e.g., vincristine, vinblastine, vindesine, paclitaxel(taxol)) bind to the cytoplasmic structural protein tubulin and prevent the assembly or disassembly of microtubules. The neuropathy associated with the use of these drugs results from their action on microtubules in the long axons of nerves.

Miscellaneous agents have diverse actions. For example, dacarbazine and procarbazine (analogs of AICA) are similar in their modes of action to the alkylating agents. Asparaginase, on the other hand, acts enzymatically.

Hormones, particularly the steroid hormones (prednisone, progesterone, estrogen) and androgen, are frequently used in cancer therapy. Other hormones that play important roles in cancer management include tamoxifen, an antiestrogen used to treat breast cancer, and leuprolide, a human gonadotropin-releasing hormone analogue, which is employed in the treatment of breast cancer and prostate cancer.

It is believed that the administration of an effective dose of antisense oligonucleotides, alone or in combination with each other or one or more of one of the above-discussed chemotherapeutic agents may completely inhibit and prevent the growth and/or spread of a variety of primary and secondary cancers in vivo in patients. When another chemotherapeutic agent is administered together with an antisense oligonucleotides, it is administered according to protocols and dosage ranges known to those skilled in the art suitable for such chemotherapeutic agent.

Preferably, for treatment for advanced ovarian cancer, the antisense oligonucleotides are used in combination with one or more alkylating agents such as cisplatin and cyclophosphamide.

The effectiveness of the treatment may be assessed by routine methods that are used for determining whether or not, for example, fertility regulation has occurred or cancer therapy has been successful.

Various modifications of the invention in addition to those shown and described herein will be apparent to those skilled in the art from the foregoing description. Such modifications are also intended to fall within the scope of the appended claims.

The foregoing disclosure includes all the information deemed essential to enable those skilled in the art to practice the claimed invention. Because the cited patents or publications may provide further useful information these cited materials are hereby incorporated by reference in their entirety.

EXAMPLES

Materials

Cell culture medium and reagents, restriction enzyme, lipofectamine, Taq DNA polymerase, Super II transcriptase, deoxynucleotides and geneticin were purchased from GIBCO (Grand Island, N.Y.). Hepes, calf thymus DNA and pregnant mare serum gonadotropin (PMSG) were from Sigma (St. Louis, Mo.). Purified human FSH was from the National Institutes of Health. RNEASE RNA extraction kits were obtained from Qiagen (Valencia, Calif.). Acrylamide, bisacrylamide, TEMED and ammonium persulfate were from Bio-Rad Laboratories (Richmond, Pa.).

The University of Cincinnati College of Medicine DNA Core Laboratories synthesized antisense and nonsense ODNs for transfection and oligonucleotide primers for reverse transcription-competitive polymerase chain reaction (RT-competitive PCR).

The full-length pFSHR cDNA and the Chinese hamster ovary cells transfected with a pure mammalian expression vector containing the cDNA for pFSHR (pFSHR-CHO cells) are prepared using conventional techniques well known in the art.

Oligodeoxynucleotides (ODNs)

We designed an 18-mer phosphorothioate antisense ODN overlapping the initiation codon of the pFSHR messenger RNA. A nonsense ODN was served as control. All sequences were compared to the GENEBANK database and found to have little homology to other kinds of cDNAs or mRNAs registered in GENEBANK.

Cell Culture pFSHR-CHO cells were maintained in Ham's F-12 culture medium supplemented with 10% fetal bovine serum, 1% L-glutamine, 10 mM hepes (pH 7.4) and 50 µg/ml geneticin. The cells were plated in 6-cm petri dishes at a density of $5 \times 10^6$ cells in 3 ml of above culture medium and cultured at 37° C. in an atmosphere of 95% air and 5% $CO_2$.

Transfection of Oligodeoxynucleotides

Two methods were designed for transfection of ODNs into pFSHR-CHO cells. 1) Direct culture: After attachment of cells to the culture dishes various concentrations (0, 5 10, 20 µM) of antisense and nonsense ODNs were added and cells were continued to culture for 24 and 48 h. 2) Liposome-DNA complex: Each 2 µg of ODNs and 12 µg of lipofectamine was diluted to 150 µl with Ham's F-12 medium without serum or antibiotics. These two diluted solutions were mixed and incubated at room temperature for 45 min. Then the liposome-ODN complex formed was added to pFSHR-CHO cells per 800 µl per dish in Ham's F-12 medium with 10% fetal bovine serum. After 5 h of incubation, 3 ml of Ham's F-12 culture medium with 10% fetal bovine serum was added and incubation was continued for 24 or 48 h.

Radioreceptor Assay

Cells were washed once with ice-cold PBS (pH 7.4), collected with a rubber policeman scraper and pelleted at 2500 rpm for 10 min. Purified hFSH was iodinated with $^{125}I$ by a modified chloramine-T method. Specific radioactivity was 10.1 µCi/µg. Cells were incubated in 500 µl assay buffer (0.15 M NaCl, 10 mM tris, pH 7.4, 0.1% BSA) for 16 h at 22° C. with $^{125}I$-hFSH (5 ng/ml) in triplicate. PMSG was added to parallel tubes in duplicate at a 2000-fold excess by mass to estimate nonspecific binding. Incubations were terminated with addition of 2.5 ml of ice-cold assay buffer followed by centrifugation (1500 g for 15 min) to pellet the cells. Bound $^{125}I$-hFSH was measured by gamma scintillation spectrometry. Nonspecific binding was subtracted from total binding to yield a specific binding.

RNA Extraction

Cells were washed twice with ice-cold 0.1 M NaCl, 0.01 M sodium phosphate, pH 7.4 (PBS). Total RNA was extracted using the Qiagen RNEASE RNA kit. Briefly, cells from one 6-cm dish were harvested with scraping and lysed in 350 µl lysis buffer and RNA was extracted according to the manufacturer's instructions. The concentrations of total RNA were determined spectrophotometrically at 260 nm.

RT-Competitive PCR

Porcine FSHR cDNA fragments which corresponded in length and sequence to the target mRNAs, except for a 20-bp insertion in the middle, was used as templates for competitive PCR (15). The competitive template was obtained by amplification of the respective cDNAs.

The first PCR amplification was carried out with the external sense primer plus internal antisense primer for synthesis of the left fragment, and with external antisense primer and internal sense primer for synthesis of the right fragment. The resulting amplification products, which contained a single overlapping region of 20 bp at their 3' ends were separated in 8% polyacrylamide gels containing 8 M urea. The cDNA bands were excised and eluted with water (100 µl). For the second PCR amplification, 5 µl of the eluate were added to a standard 100 µl PCR amplification solution containing reaction buffer, 100 nM external sense and external antisense primers, 200 µM dNTPs and 5 U Taq polymerase. Amplification was carried out as follows: 5 cycles (95° C.×1 min, 37° C.×50 sec, 72° C.×50 sec), 5 cycles (95° C.×1 min, 42° C.×50 sec, 72° C.×50 sec), 20 cycles (95° C.×1 min, 50° C.×50 sec, 72° C.×50 sec). The full-length competitive template was resolved on polyacrylamide gel, excised, eluted overnight at 4° C., precipitated and purified with 6% trichloroacetic acid and ethanol, re-dissolved in water, and quantified spectrophotometrically at 260 nm.

For reverse transcription of mRNA, total RNA (about 5 µg) was incubated with 20 µl of first strand buffer (50 mM Tris/HCl, pH 8.2, 40 mM KCl, 6 mM MgCl$_2$, 20 mM DTT), 500 µM dNTPs, 50 nM external primer, 10 U RNase inhibitor and 200 U Super II transcriptase at 42° C. for 1 h. One fifth of the resulting cDNA and increasing known concentrations of competitive template were co-amplified in 100 µl containing reaction buffer, 100 nM external sense and external antisense primers, 200 µM dNTPs and 5 U Taq polymerase. Thirty cycles of amplification were carried out as follows: 95° C.×1 min, 52° C.×50 sec, and 72° C.×50 sec.

Twenty µl of each PCR reaction product were electrophoresed in 8% polyacrylamide gels containing 8 M urea and Tris-borate/EDTA buffers (pH 8.3). Gels were stained with ethidium bromide and photographed using a digital camera. The intensities of competitive template and FSHR bands were quantified using an image analysis computer program. The ratio of the intensity of the competitive template band to the intensity of the target DNA band was graphed versus the amount of competitive template added to the sample before starting amplification. At a ratio of 1, the amount of competitive template equaled the amount of the mRNA. Because the PCR products of amplification of the competitive template were 20 bp longer than those of the target cDNA, the correction factor of 1.062 (human) and 1.071 (porcine) were used to adjust extrapolated value of FSH receptor mRNA.

DNA Quantitation

A fluorometric assay using calf thymus DNA as standard was used to quantitate cellular DNA.

Results pFSHR mRNA Content

Figure 2:
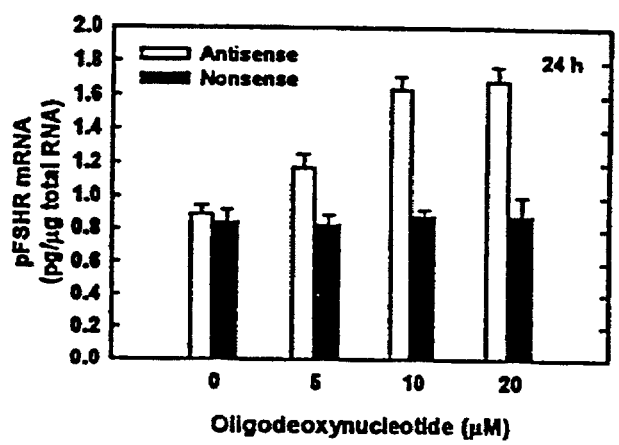
Figure 3:
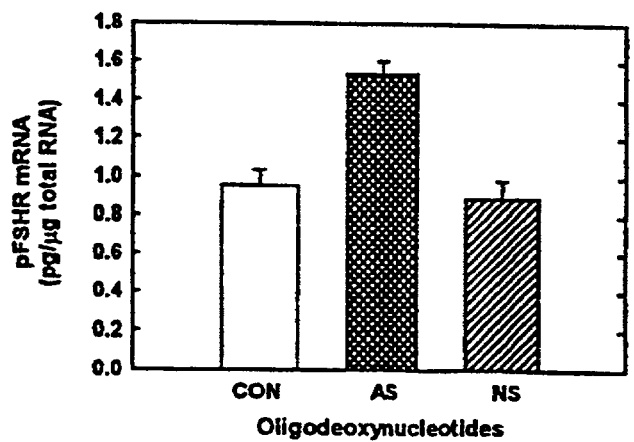
FIG. 3 Effect of ODNs added with lipofectamine on pFSHR mRNA expression in 24 h. Cells were transfected with 0.33 μM antisense ODN, nonsense ODN, or without ODNs for 24 h. Total RNA was extracted and pFSHR mRNA content was quantitated by reverse transcription and competitive polymerase chain reaction.

Controlling the abundance of a specific mRNA is one means of controlling synthesis of the protein encoded by the mRNA. Variation on mRNA contents can be achieved by alterations in the rates of both synthesis and degradation. Accurate quantitation of a particular mRNA expression is important for valid assessment of its contribution to message quantity. In the present study pFSHR mRNA contents of antisense ODN treated CHO cells were analyzed using the RT-competitive PCR method (FIG. 1). In the direct treatment of cultured cells (0-20 µM, 24 h), RT-competitive PCR results (FIG. 2) revealed an increase in pFSHR mRNA after antisense ODN application in a dose-dependent manner (1.17±0.08, 5 µM to 1.69±0.09 pg/µg total RNA, 20 µM). Compared with untreated controls (0.89±0.06 pg/µg total RNA) a clear up-regulation of the corresponding message was observable. However, no effect on mRNA levels was observed in nonsense ODN application. pFSHR mRNA contents in nonsense ODN application remained constant at 0.84±0.08 pg/µg total RNA before and after treatment. Similar results were observed in transfection with liposome-ODN complex (FIG. 3). Compared with the direct culture, the transfection with liposome-ODN complex caused an increase of mRNA contents (0.95±0.08 to 1.53±0.07 pg/µg total RNA). The results seem to indicate no significant difference was observed in pFSHR mRNA levels between direct culture of antisense ODN and transfection of liposome-ODN complex.

Binding of $^{125}$I-FSH

Figure 4:
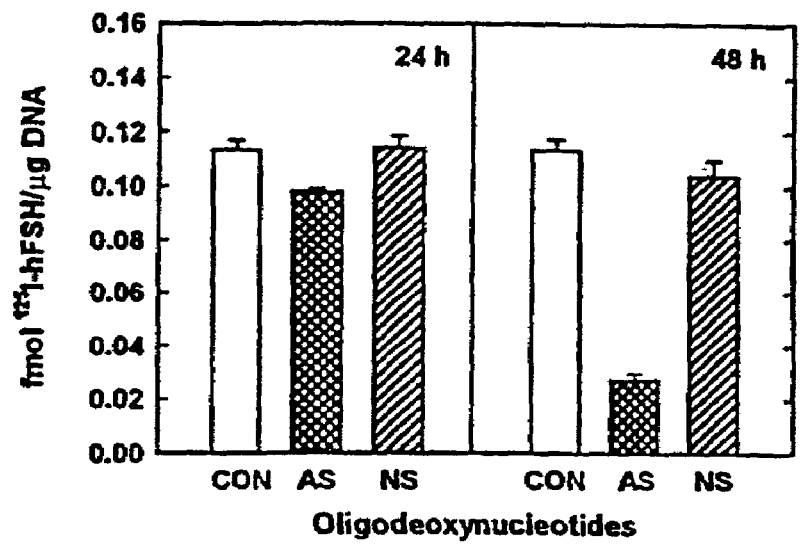
FIG. 4 Effect of ODNs on $^{125}$I-hFSH binding. Cells were cultured with 10 μM antisense ODN or nonsense ODN, or without ODNs for 24 (left) or 48 h (right). $^{125}$I-hFSH (10 ng/ml) was added to the cultures and the incubations were continued for 4 h at 37° C. Specifically bound FSH in ODN-treated cultures is expressed as fmol $^{125}$I-hFSH/μg DNA (mean±SEM, n=3).
Figure 5:
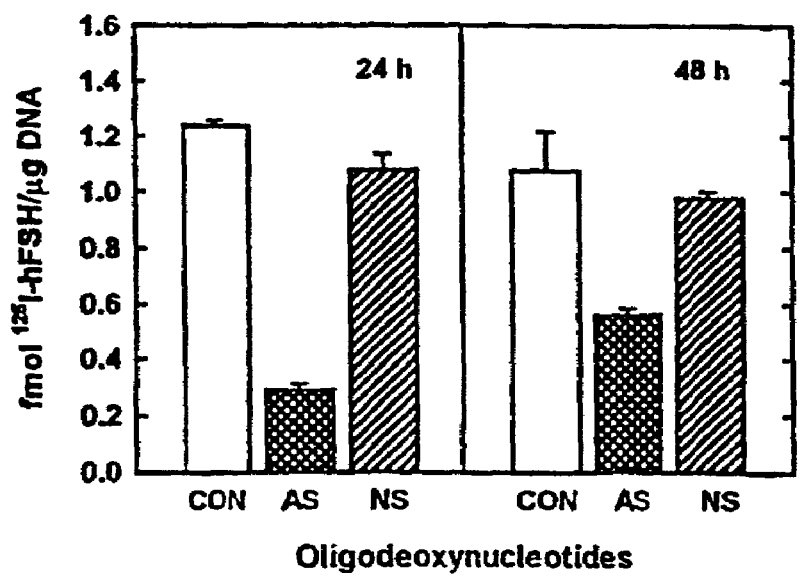
FIG. 5 Effect of ODNs added with lipofectamine on $^{125}$I-hFSH binding. Cells were transfected with 0.33 μM antisense ODN or nonsense ODN, or without ODNs for 24 (left) or 48 h (right). $^{125}$I-hFSH (10 ng/ml) was added to the cultures and the incubations were continued for 4 h at 37° C. Specifically bound FSH in ODN-treated cultures is expressed as fmol $^{125}$I-hFSH/μg DNA (mean±SEM, n=3).

The antisense ODN inhibited expression of pFSHR protein (FIGS. 4 and 5). The rapidity of the inhibitor effect was dependent on the method use to transfect the pFSHR-CHO cells. Cells that had been transfected with 10 µM antisense ODN added directly to the culture medium without lipofectamine exhibited a 13.6±0.8% (p<0.05) decrease in $^{125}$I-hFSH binding within 24 h (FIG. 4, left). In 48 h, binding was reduced 76.0±1.5% (p<0.05) (FIG. 4, right). In contrast, transfection with lipofectamine and 0.33 µM antisense ODN at 0 h caused a 76.1±1.3% (p<0.05) reduction in binding within 24 h (FIG. 5, left). Binding had returned to 52.3±2.3% (p<0.05) of normal by 48 h. (FIG. 5, right). At no time did the nonsense ODN cause a significant reduction of $^{125}$I-hFSH binding with either treatment.

What is claimed is:

1. A composition for use in regulating hormones of a host, comprising at least one antisense oligonucleotide that is complementary to a nucleotide sequence of a follicle-stimulating hormone receptor (FSHR) transcript;
   wherein the antisense oligonucleotide comprises a monomer selected from the group consisting of a deoxyribonucleoside, a ribonucleoside, an alpha-anomeric deoxyribonucleoside and an alpha-anomeric ribonucleoside;
   wherein the FSHR transcript is specific to a mammalian ovarian granulosa cell;
   wherein the antisense oligonucleotide has a nucleotide sequence capable of forming a stable duplex with a portion of the FSHR transcript wherein the portion is lying within about 50 nucleotides from the translation initiation codon of the target nucleotide sequence;
   wherein the antisense oligonucleotide is an oligomer of at least 18 nucleotide residues and is less than 60 nucleotides;
   wherein the antisense oligonucleotide comprises a sequence selected from the group consisting of SEQ ID NO: 1, SEQ ID NO:2, SEQ ID NO:3, and SEQ ID NO:4.

2. The composition of claim 1 wherein the antisense oligonucleotide is capable of forming a stable duplex with a portion of the target nucleotide sequence transcript including the translation initiation codon.

3. The composition of claim 2, wherein the antisense oligonucleotide is capable of preventing translation of the FSHR transcript upon forming a stable duplex with a portion of the FSHR transcript.

4. The composition of claim 3, wherein the antisense oligonucleotide comprises no more than one mismatch in complementarity with the transcript.

5. The composition of claim 3, wherein the antisense oligonucleotide is fully complementary to the transcript.

6. The composition of claim 3, wherein the antisense oligonucleotide is an oligomer containing at least 18 nucleotide residues and is less than 40 nucleotides.

7. The composition of claim 3, wherein the antisense oligonucleotide is an oligomer containing at least 18 nucleotide residues and is less than 30 nucleotides.

8. The composition of claim 3, wherein the antisense oligonucleotide is a phosphorothioated 18-mer antisense oligodeoxynucleotide.

9. The composition of claim 3, wherein the antisense oligonucleotide contains at least one nuclease-resistant internucleosidic linkage.

10. The composition of claim 9, wherein the internucleosidic linkage is selected from the group consisting of phosphorothioate; phosphorodithioate; phosphoramidate; methylphosphonate; P-chiral linkage, chiral phosphorothioate, phosphoroselenoate, phosphorodiselenoate, phosphoroanilothioate, phosphoranilidates, phosphotriester, aminoalkylphosphotriester, alkylphosphotriester, carbonate, carbamate, morpholino carbamate, 3'thioformacetal, and silyl.

11. The composition of claim 9, wherein the internucleosidic linkage is a phosphate analog.

12. The composition of claim 11, wherein the phosphate analog is selected from the group consisting of phosphorothioate, phosphorodithioate, phosphoramidate, and methylphosphonate.

13. The composition of claim 11, wherein the phosphate analog is a phosphorothioate.

14. The composition of claim 3, wherein the antisense oligonucleotide contains at least one substituted sugar moiety.

15. The composition of claim 3, wherein the composition includes a pharmaceutical carrier.

16. The composition of claim 15, wherein the pharmaceutical carrier contains one or more compounds selected from the group consisting of excipients, buffers, surfactants, antioxidants, hydrophilic polymers, dextrins, chelating agents, suspending agents, solubilizers, thickening agents, stabilizers, bacteriostats, wetting agents, and preservatives.

17. The composition of claim 15, wherein the composition is in the form of a pill, tablet, or capsule for oral administration to a subject in need of said compound.

18. The composition of claim 15, wherein said composition is in the form of a liquid for oral administration to a subject in need of said compound.

19. The composition of claim 15, wherein said composition being is in the form of a liquid for nasal administration as drops or spray to a subject in need of said composition.

20. The composition of claim 15, wherein said composition is in the form of a liquid for intravenous, subcutaneous, parenteral, or intraperitoneal administration to a subject in need of said composition.

21. The composition of claim 15, wherein said composition is in the form of a biodegradable sustained-release composition for intramuscular administration to a subject in need of said composition.

22. The composition of claim 3, wherein the antisense oligonucleotide is encapsulated in liposomes.

23. The composition of claim 3, wherein the antisense oligonucleotide is conjugated to poly(L-lysine) to increase cell penetration.

24. The composition of claim 3, wherein the antisense oligonucleotide is conjugated to a ligand-binding molecule.

25. The composition of claim 24, wherein the ligand-binding molecule is an antibody.

* * * * *

SEQUENCE LISTING

<160> NUMBER OF SEQ ID NOS: 4

<210> SEQ ID NO 1
<211> LENGTH: 18
<212> TYPE: DNA
<213> ORGANISM: Artificial Sequence
<220> FEATURE:
<223> OTHER INFORMATION: Artificial DNA Sequence

<400> SEQUENCE: 1
gagcagggcc ataattat                                              18

<210> SEQ ID NO 2
<211> LENGTH: 18
<212> TYPE: RNA
<213> ORGANISM: Artificial Sequence
<220> FEATURE:
<223> OTHER INFORMATION: Artificial RNA Sequence

<400> SEQUENCE: 2

```
auaauuaugg cccugcuc                                              18

<210> SEQ ID NO 3
<211> LENGTH: 18
<212> TYPE: DNA
<213> ORGANISM: Artificial Sequence
<220> FEATURE:
<223> OTHER INFORMATION: Artificial DNA Sequence

<400> SEQUENCE: 3
gagcaaggac atgattat                                              18

<210> SEQ ID NO 4
<211> LENGTH: 18
<212> TYPE: RNA
<213> ORGANISM: Artificial Sequence
<220> FEATURE:
<223> OTHER INFORMATION: Artificial RNA Sequence

<400> SEQUENCE: 4
auaaugaugu ccuugcuc                                              18
```